US00PP21035P2

(12) United States Plant Patent
Hofmann

(10) Patent No.: US PP21,035 P2
(45) **Date of Patent: *Jun. 1, 2010**

(54) **NEW GUINEA *IMPATIENS* PLANT NAMED 'FISUPNIC LI'**

(50) Latin Name: *Impatiens hawkeri*
Varietal Denomination: Fisupnic Li

(75) Inventor: Birgit Christa Hofmann, Ruedesheim (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/383,156

(22) Filed: Mar. 20, 2009

(51) Int. Cl.
*A01H 5/00* (2006.01)

(52) U.S. Cl. ..... Plt./318.6

(58) Field of Classification Search ..... Plt./318.1, Plt./318.6

See application file for complete search history.

*Primary Examiner*—Susan B McCormick Ewoldt
(74) *Attorney, Agent, or Firm*—S. Matthew Edwards

(57) ABSTRACT

A New Guinea *Impatiens* plant named 'Fisupnic Li,' particularly distinguished by the very large, round, violet-purple flowers, medium green foliage, relatively large, but narrow leaves, strong vigor, and tall, mounding plant habit with good branching.

1 Drawing Sheet

Latin name of the genus and species of the plant claimed: *Impatiens hawkeri.*

Varietal denomination: 'Fisupnic Li'.

BACKGROUND OF THE NEW PLANT

The present invention comprises a New Guinea *Impatiens*, botanically known as *Impatiens hawkeri* and hereinafter referred to by the variety name 'Fisupnic Li'.

'Fisupnic Li' is a product of a planned breeding program. The new cultivar has very large, violet-purple flowers, medium green foliage, and relatively tall plant habit.

'Fisupnic Li' originated from a hybridization made in the summer of 2004 in a controlled breeding program in Hillscheid, Germany. The female parent was an unpatented hybrid seedling identified as 'K04-4480-4' with very large purple flowers, medium green foliage and vigorous growth.

The male parent of 'Fisupnic Li' was an unpatented hybrid seedling identified as 'K04-4487-8' with purple flower color, medium green foliage, and about medium sized plant habit.

The resulting seeds were sown in the fall of 2004 in a greenhouse in Moncarapacho, Portugal, and 'Fisupnic Li' was selected there as one flowering plant within the progeny of the stated cross in about April 2005.

The first act of asexual reproduction of 'Fisupnic Li' was accomplished when vegetative cuttings were taken from the initial selection in July 2005 in a controlled environment in Moncarapacho, Portugal.

Horticultural examination of plants grown from cuttings of the plant initiated in late February of 2006 in Hillscheid, Germany, and continuing thereafter, has demonstrated that the combination of characteristics as herein disclosed for 'Fisupnic Li' are firmly fixed and are retained through successive generations of asexual reproduction.

'Fisupnic Li' has not been observed under all possible environmental conditions. The phenotype may vary significantly with variations in environment such as temperature, light intensity and day length.

Plant Breeder's Rights for this cultivar were applied for in Canada on Apr. 29, 2008 and in Switzerland on Mar. 20, 2008. 'Fisupnic Li' has not been made publicly available more than one year prior to the filing of this application.

BRIEF DESCRIPTION OF THE DRAWING

The accompanying photographic drawing shows typical flower and foliage characteristics of 'Fisupnic Li' with colors being as true as possible with an illustration of this type. The photographic drawing shows a flowering 14 week old potted plant of the new variety.

DETAILED BOTANICAL DESCRIPTION

The measurements were taken in Hillscheid, Germany, in late August 2008 on plants that were growing outdoors. Culture of these plants had started in late February 2008 when rooted cuttings were planted into 12 cm pots, placed in the greenhouse and cultivated at a minimum temperature of 16° C. In late May plants were transplanted, three each, into 45 cm diameter containers that were placed outdoors, two containers per variety were placed along the greenhouse under light rain protection.

Color chart used: Royal Horticultural Society Colour Chart (R.H.S.) 2001.

BRIEF SUMMARY OF INVENTION

The following observations, measurements, and comparisons describe plants grown outside in Hillscheid, Germany, and Chatelerault, France. The following traits have been repeatedly observed and are determined to be basic characteristics of the new variety. The combination of these characteristics distinguishes this New Guinea *Impatiens* as a new and distinct variety.

1. Uniform violet-purple flower color.
2. Very large, round flowers well above the foliage.
3. Medium green foliage, and long, narrow leaves.

4. Mounding habit, well branching.
5. Vigorous growth habit, tall in size.
6. About mid season flowering.

DIFFERENCES BETWEEN THE NEW VARIETY 'FISUPNIC LI' AND SIMILAR VARIETIES

In comparison to 'Fisnics Lil,' U.S. Plant Pat. No. 16,078, 'Fisupnic Li' has a close hue of flower color, but even larger flowers, narrower leaf shape, and distinctly taller plant size.

In comparison to 'Celebrette Grape Crush Improved,' U.S. Plant Pat. No. 14,528, 'Balcebgrapi' 'Fisupnic Li' has a somewhat less deep hue of flower color, distinctly larger flowers (2 cm larger in diameter) and taller plant habit.

Plant:
- *Form, growth and habit.*—Strong vigor, mounding plant habit, roughly semi-spherical, well-branched.
- *Plant height.*—37–40 cm.
- *Plant width.*—38–45 cm.
- *Number of branches.*—14–16.
- *Propagation.*—Terminal tips for cuttings.
- *Time to initiate and develop roots.*—18 days or less at 22° C.
- *Time to produce a finished flowering plant.*—About 10 weeks for a 12 cm pot.

Stem:
- *Color of stem.*—Brownish-purple, most intense at tips: RHS 185A, middle portion RHS 181A.
- *Length of stem.*—30–35 cm.
- *Diameter.*—0.6–0.8 cm.
- *Length of internodes.*—5–11 cm in late summer; 3–4 cm. for a young flowering plant.
- *Texture.*—Glabrous.

Foliage:
- *Arrangement.*—Mainly in whorls.
- *Growing leaf, color upper surface.*—RHS 143A to RHS 144A.
- *Growing leaf, color lower surface.*—RHS 138B.
- *Mature leaf, color, upper surface.*—RHS 137B.
- *Mature leaf, color lower surface.*—RHS 138B.
- *Length.*—12–15 cm.
- *Width.*—About 3.7–4.5 cm.
- *Shape.*—Elliptical, relatively narrow.
- *Base shape.*—Acute.
- *Apex shape.*—Acuminate.
- *Margin.*—Slightly serrate, ciliate.
- *Texture.*—Slightly rugose, slightly glossy surface.
- *Color of veins, upper surface.*—Reddish, RHS 53B near base, fading towards the tip
- *Color of veins, lower surface.*—Purple-red, RHS 60A.

Petiole:
- *Color upper surface.*—RHS 53A to 53B.
- *Color lower surface.*—RHS 60A.
- *Length.*—2.0–3.0 cm.
- *Diameter.*—3–4 mm.
- *Texture.*—Mainly glabrous.

Inflorescence:
- *Duration of flowering.*—Continuous flowering from spring through fall, in the greenhouse year round depending on light intensity.
- *Blooming habit, start.*—About 10 weeks after planting of rooted cuttings.
- *Inflorescence type.*—Flowers appear solitary in the leaf axils of the upper nodes of the stems.
- *Number of flowers per node.*—About 4–6 flowers and buds in various stages of development.
- *Number of flowers per plant.*—17–20.
- *Flowering season.*—Continuously, mainly from March to October, depending on light intensity.
- *Lastingness of individual blooms.*—About 8–10 days (18° C., greenhouse in spring time).

Pedicel:
- *Color.*—RHS 185A.
- *Length.*—Most often 5.0–6.0 cm.
- *Diameter.*—1 mm.
- *Texture.*—Flexible, glabrous.

Flower:
- *Form.*—Single-type, 5 petals.
- *Shape of corolla.*—Round, flat, with overlapping petals.
- *Overall color.*—Violet-purple, uniform.
- *Upper surface.*—RHS N74A.
- *Markings.*—No markings, no real eye zone.
- *Lower surface.*—RHS N74B.
- *Length of flower.*—9.0 cm.
- *Width of flower.*—8.5 cm.
- *Depth.*—1.0–1.2 cm.

Petals:
- *Shape.*—Obcordate.
- *Apex shape.*—Emarginate.
- *Base.*—Attenuate.
- *Margin.*—Entire.
- *Petal size.*—Upper (banner) petal, length: 3.7–3.8 cm. Upper petal, width: 6.4 cm. Lateral petals, length: 4.0–4.2 cm. Lateral petals, width: 4.5 cm. Lower petals, length: 4.2 cm. Lower petals, width: 5.0–5.2 cm.
- *Petal texture.*—Smooth, glabrous.

Spur:
- *Position and shape.*—Elongate, bending downwards.
- *Color.*—R.H.S.
- *Length.*—6.0–6.5 cm.
- *Diameter.*—0.3 cm at base.

Bud (just before opening):
- *Shape.*—Ovoid.
- *Length.*—2.3 cm.
- *Diameter.*—1.6 cm.
- *Color.*—RHS N74A.

Calyx:
- *Number of sepals.*—4–5, of the upper one fused with the underside of the banner petal, 2 lateral sepals, and a large sepal (2 fused sepals) bearing the spur.
- *Color of lateral sepals.*—RHS 180C.
- *Shape of lateral sepals.*—Ovoid with acuminate tips.
- *Length of lateral sepals.*—1.6–1.7 cm.
- *Width of lateral sepals.*—0.7 cm.
- *Color of large sepal.*—Pink, mainly RHS 55C.
- *Shape of large sepal.*—Ovoid with cuspidate tip.
- *Length of large sepal.*—1.9 cm.
- *Width of large sepal.*—1.5 cm.
- *Margins.*—Entire.
- *Texture.*—Glabrous.

Reproductive organs:
- *Pistil.*—One.
- *Length.*—0.6 cm.
- *Ovary shape.*—Elongate, 0.6 cm.
- *Color of ovary.*—Grass-green, RHS 144A initially, later RHS 146A.
- *Style and stigma.*—Very short, in a ring on top of the ovary.
- *Style and stigma color.*—Yellowish, RHS 13D.

*Androeceum.*—5 stamen, fused, the anthers hooded.

*Diameter of androeceum.*—0.6–0.7 cm.

*Surface color.*—Rose-red, between RHS N57B and N57C.

*Pollen amount.*—Moderate.

*Color of pollen.*—RHS 8D (whitish-yellow).

*Fertility/seed set.*—No seed set observed.

Disease/pest resistance: Disease resistance or susceptibility has not been observed on this hybrid.

What is claimed is:

1. A new and distinct variety of New Guinea *Impatiens* plant named 'Fisupnic Li,' substantially as illustrated and described herein.

* * * * *

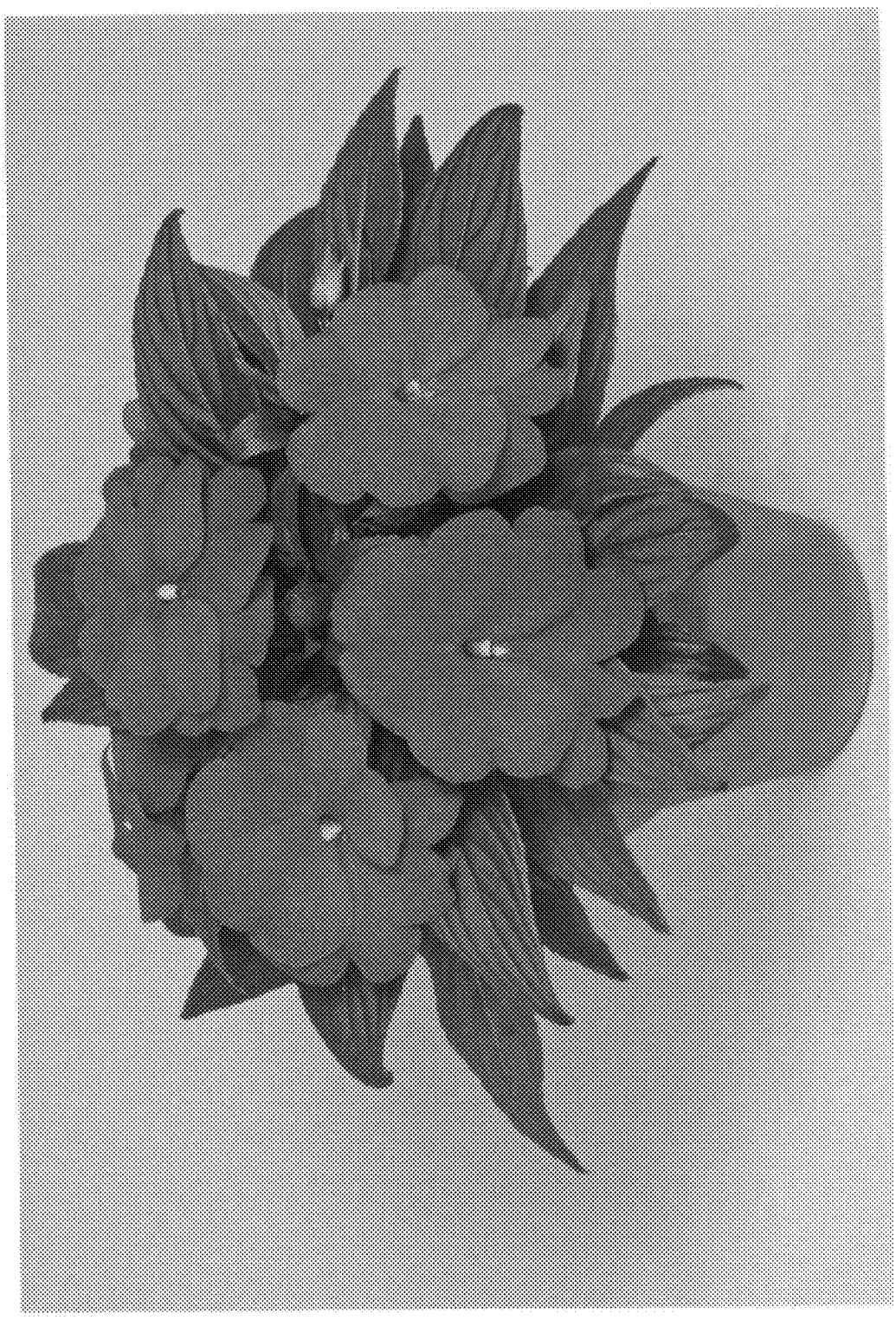

UNITED STATES PATENT AND TRADEMARK OFFICE

CERTIFICATE OF CORRECTION

PATENT NO. : PP 21,035 P2
APPLICATION NO. : 12/383156
DATED : June 1, 2010
INVENTOR(S) : Hofmann It is certified that error appears in the above-identified patent and that said Letters Patent is hereby corrected as shown below:

Column 4, line 35, delete "R.H.S." and insert therefor --RHS 53A to RHS 53B--

Signed and Sealed this

Third Day of August, 2010

David J. Kappos

David J. Kappos
*Director of the United States Patent and Trademark Office*